United States Patent
Shalaby et al.

(10) Patent No.: US 7,981,945 B2
(45) Date of Patent: Jul. 19, 2011

(54) ANTIMICROBIAL, RADIOPAQUE, MICROFIBER-REINFORCED, POLYMERIC METHACRYLATE BONE CEMENT

(75) Inventors: Shalaby W Shalaby, Anderson, SC (US); Michael Scott Taylor, Pendleton, SC (US)

(73) Assignee: Poly-Med, Inc., Anderson, SC (US)

( * ) Notice: Subject to any disclaimer, the term of this patent is extended or adjusted under 35 U.S.C. 154(b) by 241 days.

(21) Appl. No.: 12/223,211

(22) PCT Filed: Feb. 6, 2007

(86) PCT No.: PCT/US2007/003045
§ 371 (c)(1),
(2), (4) Date: Jul. 24, 2008

(87) PCT Pub. No.: WO2007/106256
PCT Pub. Date: Sep. 20, 2007

(65) Prior Publication Data
US 2010/0152319 A1    Jun. 17, 2010

(51) Int. Cl.
*A61F 2/00* (2006.01)
(52) U.S. Cl. ........................................................ 523/117
(58) Field of Classification Search ................... 523/117
See application file for complete search history.

(56) References Cited

U.S. PATENT DOCUMENTS

| | | |
|---|---|---|
| 3,715,331 A | 2/1973 | Molnar |
| 4,191,740 A * | 3/1980 | Heusser et al. ............. 424/489 |
| 4,404,327 A | 9/1983 | Crugnola et al. |
| 4,456,711 A | 6/1984 | Pietsch et al. |
| 4,500,658 A | 2/1985 | Fox |
| 4,535,485 A | 8/1985 | Ashman |
| 4,547,390 A | 10/1985 | Ashman |
| 4,791,150 A | 12/1988 | Braden |
| 5,508,342 A * | 4/1996 | Antonucci et al. ............. 524/788 |
| 5,795,922 A | 8/1998 | Demian et al. |
| 2004/0013873 A1 * | 1/2004 | Wendorff et al. ............. 428/364 |
| 2004/0029996 A1 * | 2/2004 | Kuhn ............................. 523/116 |
| 2004/0236424 A1 * | 11/2004 | Berez et al. ................ 623/14.12 |
| 2005/0027034 A1 * | 2/2005 | Bond et al. .................... 523/118 |

FOREIGN PATENT DOCUMENTS

WO    WO 2005009481 A2 *    2/2005

OTHER PUBLICATIONS

Gilbert et al, 1995, "Sefl-reinforced composite poly(methyl methacrylate): static and fatigue properties", Biomaterials, vol. 16, p. 1043-1055.*
English machine translation of WO Patent Pub No. 2005009481 A2, Nies et al, Feb. 3, 2005.*
Gilbert et al, 1995, "Self-reinforced composite poly(methyl methacrylate): static and fatigue properties", Biomaterials, vol. 16, p. 1043-1055.*
Buckley C.A. et al, "Thermomechanical processing of PMMA into high strength fibers," J. Appl. Polym. Sci., 44, 1321, 1992.
Gilbert et al, "Self-reinforced composite poly(methyl methacrylate): static and fatigue properties," Biomaterials, 16, 1043, 1995.

* cited by examiner

*Primary Examiner* — Mark Eashoo
*Assistant Examiner* — David Karst
(74) *Attorney, Agent, or Firm* — McCormick, Paulding & Huber LLP

(57) ABSTRACT

An methacrylate bone cement is toughened and rendered radiopaque by reinforcing with electrospun microfibers including a radiopacifier and antimicrobial agents to provide a bone cement for use in repairing bone or other hard tissues.

19 Claims, No Drawings

ANTIMICROBIAL, RADIOPAQUE, MICROFIBER-REINFORCED, POLYMERIC METHACRYLATE BONE CEMENT

FIELD OF THE INVENTION

This invention relates to an antimicrobial methacrylate bone cement that is toughened and rendered radiopaque by reinforcing with electrospun microfiber having a radiopacifying component in the form of micro-/nanoparticulate inorganic materials or organometallic ionic conjugates of a metallic ion, wherein the bone cement exhibits antimicrobial properties for managing bone infection by incorporating at least one type of micro-/nanoparticulate antimicrobial agent.

BACKGROUND OF THE INVENTION

As used in the medical field, a bone cement generally refers to a biocompatible material that can be used to repair damaged or diseased bone or other hard tissues. Specifically, bone cement is used to fill voids or gaps in bones, to affix or anchor an orthopedic implant in a prepared area of the body, or to repair or replace damaged or diseased teeth. Ideally, the bone cement closely assimilates the mechanical characteristics of the hard tissue that the cement is intended to repair or replace.

In most applications, bone cement is made from an acrylic polymeric material. Typically, the bone cement is comprised of two components: a dry or powder component and a liquid component, which are subsequently mixed together to form a resulting cured cement. The dry component of a bone cement system generally includes an acrylic polymer, such as polymethyl methacrylate (PMMA). The PMMA is typically present in the form of small polymer beads, but can also appear in the form of amorphous particles. Regardless, the PMMA powder generally has the consistence of flour. In addition to the acrylic polymer, a polymerization initiator, such as benzoyl peroxide, can also be added to the powder component for the purpose of later initiating the free-radical polymerization process. The polymerization initiator can be added as small particles or can be incorporated into the beads made from the polymer. The liquid component, on the other hand, typically contains a liquid monomer that is mixed with the corresponding acrylic polymeric powder. One example of a liquid monomer is methyl methacrylate (MMA). The liquid component can also contain an accelerator, such as an amine (e.g., N,N-dimethyl-p-toluidine). A stabilizer, such as hydroquinone, can also be added to the liquid component to prevent premature polymerization of the liquid monomer. When the liquid component is mixed with the powder or dry component, initially, the liquid monomer wets the polymeric powder. Since the powder (PMMA) is soluble in the liquid monomer, the solid polymer beads partially begin to dissolve or swell in the liquid monomer. The polymerization reaction starts as soon as the two components are mixed. The amine accelerator reacts with the initiator to form free radicals which begin to link monomer units to form polymer chains intermixed with the dissolved portion of the polymer powder. In the next two to four minutes, the polymerization process proceeds, changing the viscosity of the mixture from a syrup-like consistency (low viscosity) into a dough-like consistence (high viscosity). In this state, the bone cement is applied to a prepared area of the body where it is to be used. Ultimately, further polymerization and curing occur until the cement is fully hardened. Typically, it takes anywhere from about 5 minutes to about 20 minutes for the bone cement to fully cure after the two components are mixed. Since the polymer beads only partially dissolve during mixing, the resulting solid includes a dispersion of polymeric beads contained in a matrix of the acrylic polymer.

Although bone cement is widely utilized in a variety of orthopedic and dental applications, its glassy, amorphous nature as a thermoplastic material is responsible for its relatively low strength if used in load-bearing applications. This, and the high glass transition temperature ($T_g$) of PMMA are associated with its poor fatigue performance. The presence of the porosity and other stress concentration sites introduced during application contributes further to the weakness of PMMA bone cement. In fact, fatigue fracturing has been found to be one of the main causes for the loosening and cement fragmentation during the long-term use of the traditional PMMA bone cement. Although a few techniques have been used to address the shortcomings associated with the PMMA, long-term cement fatigue is yet to be circumvented.

To improve the mechanical properties of PMMA bone cement, in general, certain aspects of the composite technology have been explored. For example, fibers made of carbon, steel, KEVLAR, ultrahigh molecular weight polyethylene (UHMW-PE) and titanium have been incorporated into the PMMA matrix as reinforcing fillers to improve its mechanical properties. Although these composites did show some improvement in mechanical properties, such as fracture toughness and fatigue resistance, the incompatibility between fibers and matrix posted possible weak interfacial bonding. To overcome the problems with the traditional composites, a new composite technology was developed which uses PMMA fibers as a fillers to produce the self-reinforced PMMA composites. While commercial PMMA in bulk form has a strength of about 50 MPa and a breaking elongation of about 5%, PMMA fibers having a strength of 220 MPa, modulus of 8 GPa, and a breaking elongation of 25% were successfully prepared by melt extrusion and drawing (Buckley, C. A., Gilbert, J. L. and Lautenschlager, E. P., Thermomechanical processing of PMMA into high strength fibers, *J. Appl. Polym. Sci.*, 44, 1321, 1992). Such fibers are highly oriented. Because of the increased elongation at break, the PMMA fibers resulted in a significant improvement in ductility of the self-reinforced composite compared to single-component polymer. Using PMMA fibers, Gilbert et al prepared self-reinforced PMMA composites with a 60% fiber fraction and tested their mechanical properties (Gilbert, J. L., Ney, D. S. and Lautenschlager, E. P., Self-reinforced composite poly(methyl methacrylate): static and fatigue properties, *Biomaterials*, 16, 1043, 1995). The results indicated that although the modulus of composites showed a limited increase in comparison to pure PMMA, the ultimate elongation increased significantly, suggesting high toughness for the self-reinforced PMMA composites. The single edge notched tests showed an increase of almost 100% in fracture toughness for composites. The study of failure mechanisms revealed that the composites absorbed much energy before fracture. Fatigue experimental results showed that the composites had significant fatigue strength improvement over that of bulk PMMA. It was claimed that the fiber-matrix bond in self-reinforced PMMA composites is uniform and continuous through the composite.

Perhaps the most common application for bone cement is in the fixation of prosthetic devices. Prosthetic devices are artificial materials used to replace or strengthen a particular part of the body. When implanting a prosthesis, first a receiving site or cavity is prepared in an adjoining bone. In particular, the bone can be cut and reamed out in order to accommodate the prosthesis. A bone cement is then mixed and placed in the receiving site or cavity. A prosthesis is positioned in the bone cement and the bone cement is hardened affixing the prosthesis to the bone.

The above process for implanting a prosthetic device is generally accepted within the art and has proven to be a successful one for repairing or replacing damaged bones and the like. Prosthetic devices, however, can be prone to loosening within the bone cavity over time. In particular, the acrylic bone cement has been universally considered the weakest link in the implant design. Most bone cements are neither as strong nor as flexible as bone tissues. Consequently, the bone cement can break away from the prosthesis, can fracture, or can develop fatigue cracks when exposed to repeated loads. Because problems can develop in the bone cement mantle or bed surrounding a prosthesis, it is important that the condition of the implant be monitored after surgery. However, bone cement, like most polymers, is relatively radiolucent, meaning that the bone cement is transparent to X-rays. Consequently, in order to inspect the bone cement mantle postoperatively, radiopacifiers are commonly added to the dry component of a bone cement system in a sufficient amount to give the resulting bone cement the necessary radiopacity for examination by X-rays. Unfortunately, radiopacifiers, such as barium salts and certain metal oxides, when added to bone cement, tend to reduce the mechanical properties of the cement. Radiopacifiers, which have a higher density and polarity than the polymeric material they are mixed with, tend to collect together and clump or agglomerate in the bone cement. These agglomerates have been shown to act as stress concentration sites and have been shown to decrease the ultimate flexural strength, intrinsic tensile strength, fatigue strength, as well as the fracture toughness of the cement. Due to these deficiencies, many of those skilled in the art have attempted to improve the mechanical properties of radiopaque bone cements. For instance, in U.S. Pat. No. 4,500,658 to Fox, a radiopaque acrylic resin is disclosed. Specifically, a radiopaque inorganic pigment is distributed in the polymer beads that are incorporated into the bone cement. The polymer beads incorporating the pigment are formed by suspension polymerization. U.S. Pat. No. 4,791,150 to Braden, et al. also teaches incorporating particles of an opacifier into the polymer beads. By incorporating the opacifier particles into polymer beads, the particles will remain trapped within the beads during formation of the bone cement, preventing the particles from forming agglomerates in the polymer matrix. U.S. Pat. No. 5,975,922 to Damian, et al. teaches the use of a radiopacifier that is microencapsulated with a bone cement compatible material. When combined with the liquid monomer, the bone cement compatible material dissolves releasing the radiopacified particles into a bone cement matrix. By being microencapsulated, the radiopacifier is prevented from agglomerating in the cement. Instead, the radiopacifier particles become dispersed through the bone cement matrix, which not only creates a radiopaque cement, but also increases the fatigue life of the cement. Other bone cement materials containing radiopacifiers are disclosed in U.S. Pat. No. 4,547,390 (Ashman, et al.); U.S. Pat. No. 4,535,485 (Ashman, et al.); U.S. Pat. No. 4,456,711 (Pietsch, et al.); U.S. Pat. No. 4,404,327 (Cruganola); and U.S. Pat. No. 3,715, 331 (Molnar). Although U.S. Pat. No. 5,795,922 provides a scientifically viable solution to the problem of clustering or agglomerating radiopacifier particles, the use of the complex and costly microencapsulation technology to pre-encase the radiopacifier particles to prevent clustering is technologically impractical and economically forbidding. This provided an incentive to explore novel approaches to prevent the radiopacifier from aggregation or clustering using technologically and economically feasible methods as provided by the present invention.

Different types of antibiotic-loaded PMMA bone cements are used extensively for treatment and prophylaxis of bone infection. In most cases, manufacturers make their own antibiotic bone cements by simply mixing solid antibiotic particles with the PMMA powder component of plain bone cement (K-D. Kühn, Bone Cements, Springer, N.Y., 2000, p. 149.). Most commonly incorporated antibiotics, such as gentamicin, tobramycin, are used as water soluble salts, which makes them physically incompatible with the hydrophobic component of the PMMA plain cement. This and the fact that they are mixed with the solid PMMA powder results in their presence as agglomerates in the cured cement. This results in having unevenly distributed, relatively large antibiotic aggregates, which (1) compromise the mechanical properties of the cement; (2) interfere with timely and prolonged release of the drug at predictable rates; and (3) require an increase of the initial concentration of the drug for attaining early clinical efficacy. These limitations created a need to explore a new approach to incorporate antibiotics in the bone cement to circumvent the noted limitations. And this invention deals with a new method for producing bone cements with evenly distributed antibiotic agents in a molecular form or as micro-/nanoparticles.

SUMMARY OF THE INVENTION

This invention generally deals with an antimicrobial, radiopaque, microfiber-reinforced, toughened polymeric methacrylate bone cement which is a polymeric methacrylate matrix reinforced with electrospun microfibers, wherein the microfibers are electrostatically spun from a methacrylate polymer solution containing at least one antimicrobial agent and at least one micro-/nanoparticulate radiopacifier. The polymer solution from which the fibers are spun includes at least one organic solvent selected from the group consisting of chloroform, dichloromethane, acetonitrile, acetone, and tetrahydrofuran. And a surfactant such as TWEEN-20 or -80 (polyoxyethylene sorbitan monooleate) is also included.

Another aspect of this invention deals with an antimicrobial, radiopaque, microfiber-reinforced, toughened polymeric methacrylate bone cement which is a polymeric methacrylate matrix reinforced with electrospun microfibers, wherein the microfibers are electrostatically spun from a methacrylate polymer solution containing at least one antimicrobial agent, at least one micro-/nanoparticulate radiopacifier, a surfactant and a second polymer. The second polymer can be an aliphatic polyester such as poly-$\epsilon$-caprolactone.

Another specific aspect of this invention pertains to an antimicrobial, radiopaque, microfiber-reinforced, toughened polymeric methacrylate bone cement which is a polymeric methacrylate matrix reinforced with electrospun microfibers, wherein the microfibers are electrostatically spun from a methacrylate polymer solution containing at least one antimicrobial agent, and at least one micro-/nanoparticulate radiopacifier, wherein the radiopacifier is at least one selected from a metal oxide, barium sulfate, basic bismuth carbonate, bismuth glass, and zirconium dioxide. Furthermore, the antimicrobial agent is at least one agent selected from clindamycin hydrochloride, erythromycin-glucoheptonate, gentamicin sulfate, vancomycin, and tobramycin. Preferably, the methacrylate polymer matrix is formed by free-radical polymerization, using a free-radical initiator and an amine-type activator, of at least one liquid methacrylate monomer selected from methacrylic acid, methyl methacrylate, ethyl methacrylate, isobutyl methacrylate, hexyl methacrylate, hydroxyethyl methacrylate, and octyl methacrylate. It is understood that the free-radical initiator can be benzoyl peroxide or di-t-butyl peroxide and the amine-type activator can be N,N-dimethyl-p-toluidine. In one embodiment the liquid methacrylate monomer is hydroquinone.

A key aspect of this invention deals with an antimicrobial, radiopaque, microfiber-reinforced, toughened polymeric methacrylate bone cement which is a polymeric methacrylate matrix reinforced with electrospun microfibers, wherein the microfibers are electrostatically spun from a methacrylate polymer solution containing at least one antimicrobial agent and at least one micro-/nanoparticulate radiopacifier, wherein the methacrylate polymer from which the microfibers are electrostatically spun is formed by the free-radical polymerization of a combination of N-vinyl pyrrolidone, methyl methacrylate and one additional monomer selected from hexyl methacrylate, methacrylic acid, isobutyl methacrylate, and octyl methacrylate. Preferably the electrostatically spun microfibers are in the form of a microfibrous construct selected from a non-woven flat fabric, rovings of non-woven yarn, ground entangled microfibers with an average microfiber length of less than 1 mm and compressed dense sheets of entangled microfibers having an average thickness of less than 0.5 mm.

Furthermore, the method for preparing such bone cement includes the steps of:
  a. rinsing the electrostatically spun microfiber construct with cold water;
  b. drying the microfiber construct;
  c. mixing the microfiber construct with 80 percent of the liquid methacrylate matrix monomer, such liquid monomer containing a free radical initiator;
  d. mixing the premixed combination from step "c" with the remaining 20 percent of the liquid methacrylate matrix monomer, the remaining 20 percent of the liquid monomer containing an activator;
  e. transferring the mixture from "d" to an application site; and
  f. allowing the composite to cure, preferably at 37° C.

A technologically relevant aspect of this invention deals with an antimicrobial, radiopaque, microfiber-reinforced, toughened polymeric methacrylate bone cement which is a polymeric methacrylate matrix reinforced with electrospun microfibers, wherein the microfibers are organometallic microfibers, and wherein the organometallic microfibers are electrospun from methacrylate copolymer having reactive carboxylate groups ionically conjugated with barium ions.

Another general aspect of this invention deals with an antimicrobial, radiopaque, microfiber-reinforced, toughened polymeric methacrylate bone cement which is a polymeric methacrylate matrix reinforced with electrospun microfibers, wherein the cement is a polymeric methacrylate matrix reinforced with electrostatically spun, antimicrobial, radiopaque microfibers of a methacrylate polymer and at least one low glass transition polyester made by condensation polymerization of a dihydroxy compound and diester. Alternatively the low glass transition polyester can be made by the ring-opening polymerization of at least one cyclic monomer selected from ε-caprolactone, l-lactide, trimethylene carbonate, p-dioxanone, glycolide, and a morpholine dione. The polymer blend from which the microfibers are spun further contains at least one antimicrobial agent and at least one micro-/nanoparticulate radiopacifier.

DETAILED DESCRIPTION OF PREFERRED EMBODIMENTS

Plane PMMA bone cements have been used extensively in many dental and orthopedic applications without significant change in their composition or method of application since their first introduction in the early 1970s. This is in spite of consistently reported concerns about their clinically, less-than-optimal performance, particularly when used in load-bearing applications such as in articulating joint replacements. Most of the concerns centered about (1) excessive and sometime unpredictable heat generation during application at the intended site and associated tissue necrosis; (2) inadequate cement uniformity due to improper mixing of cement components, resulting in product non-uniformity and frequent presence of air pockets and cement porosity, which, in turn, lead to formation of stress concentration sites that contribute to poor fatigue endurance and long-term mechanical failure and hence, loosening implants as in the case of cemented prosthetic joints; (3) perioperative infection which may require removal of cemented implants due to bone infection; and (4) migration of the methyl methacrylate monomer from the application site leading to so-called cement disease, especially in the case of cement hip prosthesis. Regrettably, many attempts have been made by several investigators to address these drawbacks with limited or no success. Such attempts of the prior art included those dealing with (1) improving the mixing method of the cement components and application of vacuum to remove air bubbles—this proved to be operator-dependent and interfered with attaining a flowable cement paste for a timely application; (2) microencapsulating the radiopacifier particles to prevent their aggregation resulting in more uniform cement with higher fatigue endurance—this is recognized as technologically impractical and costly; (3) incorporating solid antibiotics into the solid component of the cement to prevent perisurgical infection and possibly treating post-surgical infection—this appears to contribute negatively to the problem of cement non-uniformity and associated compromise of long-term mechanical properties; and (4) self-reinforcing the PMMA matrix with melt-spun, drawn fibers to increase the cement modulus—this appeared to impair the mixing process, leading to cement non-uniformity under typical clinical settings. Failure or limited success of the numerous attempts of the prior art to truly optimize the composition and application method of the plane PMMA cement and antibiotic-loaded PMMA bone cement provided the incentive to pursue the present invention, which deals, in general, with an antimicrobial, radiopaque, microfiber-reinforced, toughened, polymeric methacrylate bone cement comprising a polymeric methacrylate matrix reinforced with electrospun microfibers and methods for formulating and delivery of the cement to the application site. A pivotal aspect of the present invention deals with the preparation and use of electrostatically spun (or electrospun) microfibers for reinforcement, wherein the microfibers contain micro-/nanoparticulate radiopacifier of radiopacifying metal ion conjugated to an anion-bearing methacrylate copolymeric chain. Another pivotal aspect of this invention deals with the use of at least one antibiotic compound selected from water soluble salts or forms of doxycycline, tetracycline, gentamicin, tobramycin, clindamycin, vancomycin, and analogs thereof as micro-/nanoparticles dispersed in the electrospun microfibers or as a component of an ionic conjugate with an anion-bearing or anion-forming copolymeric chain of the microfibers. The electrospun microfibers can be formed by electrospinning a polymer solution in a volatile solvent containing a microdispersion of micro-/nanoparticles of the radiopacifier and the antibiotic. Alternatively, the polymer solution may be selected to be capable of dissolving the antibiotic and hence, the electrospinning system can contain at least one soluble antibiotic and a micro-/nanoparticle dispersion of the radiopacifier. A specific aspect of this invention deals with the electrospinning of a solution of anion-bearing or anion-forming methacrylate copolymer containing the micro-/nanoparticulate radiopacifier wherein the resulting microfibers are treated with an aqueous solution of at least one water-soluble antibiotic to ionically immobilize/bind the antibiotic onto the surface of the microfiber. This permits a facile, early release or burst of the antibiotic at the application site and sustained release thereafter. Another specific aspect of this invention deals with an electrospun carboxyl-bearing methacrylate copolymer and subsequent ionic immobilization of a radiopacifying metallic ion and at least one antibiotic onto the surface of the electrospun fibers. The anion-forming methacrylate copolymeric chain or its polymeric precursor can be made by the free-radical polymerization of methyl methacrylate with methacrylic acid, itaconic anhydride, and/or maleic anhydride, wherein the anhydride groups are hydrolyzed to yield the respective carboxylic side groups needed for the ionic binding of metallic ions such as $Ba^{+2}$ or basic/amphoteric antibiotic. Prior to ionically binding the $Ba^{+2}$ and/or basic/amphoteric antibiotic, the acidic side groups of the copolymeric chain can be treated with a dilute solution of a sodium or potassium carbonate to maximize the ionic conjugation of (1) the $Ba^{+2}$, for instance, from an aqueous solution of $BaCl_2$ or $BaNO_3$; and/or (2) the antibiotic salt present as an aqueous solution. Furthermore, to create an acidic functionality on the PMMA chain, the polymer can be partially sulfonated, phosphonylated (followed by hydrolysis of the phosphonyl chloride group) to produce sulfonic acid or phosphonic side groups prior to its electrospinning, thus yielding microfibers with active sites for binding metallic radiopacifying ions and/or basic as well as amphoteric antibiotics.

A key aspect of this invention deals with using microfibers having an average diameter of less than 20 microns and preferably less than 15 microns and more preferably less than 10 microns as high-surface-area reinforcing fillers for the PMMA matrix, thus insuring a maximized filler-matrix interfacing leading to a more intimate interface than that of the prior art where melt-spun fibers having a diameter of more than 50 microns and most likely more than 100 microns, with far less surface/volume ratios were used.

A clinically relevant aspect of the present invention deals with the use of a mixture of a methacrylate polymer and a low $T_g$ polyester such as polycaprolactone for electrospinning, which permits the formation of a toughened cement by virtue of having the high compliance component, present in the PMMA cement, which acts as a toughening agent. The amount of the low $T_g$ polyester can be adjusted to yield bicomponent microfibers having a polyester-rich surface with controlled solubility in the liquid methyl methacrylate (MMA) and hence, allow the microfibers to exhibit maximum reinforcing effect. Toughening of the PMMA matrix can be achieved by incorporating methacrylate comonomers having long paraffinic side groups. This also slows down the rate of polymerization and hence, reduces the heat generation during curing. Another clinically relevant aspect of this invention deals with the use of a bioabsorbable low $T_g$, high compliance polyester in the electrospinning solution of PMMA to produce partially absorbable microfibers—as the absorbable component of the cement undergoes degradation on the surface, bone-tissue ingrowth prevails leading to implant/bone osseointegration and ultimate implant stabilization. Another useful feature of having an absorbable component in the cement pertains to regulating the release of the antibiotic from the bulk of the cement for long-term use.

A clinically unique feature of the bone cement, subject of this invention, deals with the ability of placing the reinforcing microfiber component at the implant site and injecting or pouring the liquid component there onto it. This insures a maximum integration of the forming matrix with the reinforcing microfibers through a situation similar to static mixing. This also eliminates the problem associated with the dynamic mixing of reinforcing fibers having traditional diameter of the prior art. For use in connecting artificial joints and other similar prostheses where the monomer migration is a possible problem, the electrospun microfibers can be used as a plug to restrict or prevent the flow of the monomer from the application site—this, for instance, eliminates the need for using a bone plug as in the case of hip joint prosthesis. Additionally, the liquid monomer can be mixed with an ultrahigh molecular weight PMMA to increase its viscosity and prevent monomer migration through the microfibrous plug. An interesting feature of the present invention is associated with use of high-surface-area microfibers reinforcing components with an evenly distributed polymerization catalyst throughout its bulk and surface, coupled with the static mixing feature noted above. This results in a controlled, uniform polymerization with no localized hot spots. This provides a solution to the problem of excessive and sometimes localized heat generation and associated tissue necrosis during cement curing. In recent years, the controversial use of antibiotic-loaded cement as antibiotic spacers has increased significantly. Meanwhile, the present inventive antimicrobial bone cement compositions, when taken with the ability to control the heat of polymerization and release profile of the drug, represent a clinically important advancement that nullifies existing objections to the use of antibiotic-loaded bone cement as antibiotic spacers.

Further illustrations of the present invention are provided by the following examples:

EXAMPLE 1

Preparation of <5μ $BaSO_4$ Particles

Powdered $BaSO_4$ was obtained. The powder was freeze-milled (SPEX 6850 Freeze/Mill) for not less than 3 cycles, 2 minutes long at 10 hz. A sieve with 5 um square grating (Precision Eforming, LLC) was used in an acetone medium to separate particles smaller than 5 um in diameter. Resulting acetone/$BaSO_4$ mixture was centrifuged and the $BaSO_4$ pellet was removed and dried under room temperature vacuum.

EXAMPLE 2

PMMA with $BaSO_4$, Low Concentration

To produce a 10:1 PMMA:$BaSO_4$ (wt./wt.) electrospun fabric, a solution was made in two components. In Jar 1, 10.0 g PMMA ($M_n$=996 kDa) was mixed with 17 mL chloroform and 17 mL dichloromethane. This jar was rolled until a homogenous solution was formed. In Jar 2, 1 g of $BaSO_4$ (<5 um particles, as prepared above) was mixed with 17 mL Chloroform and 220 mg Tween-80 to assist in the separation of particles. This jar was sonicated for a minimum of 1 hour to assure deagglomeration of particles. Just before spinning, Jar 2 was added to Jar 1 and rolled until well mixed (~5 minutes). The solution was electrospun on an electrospinning apparatus assembled in-house with the following conditions:
- 20-gauge blunt-end needle
- 0.07 mL/min flow rate
- +17 kV needle
- +10 kV directional rods to help direct fiber path
- Grounded collector
- 10" needle to collector distance To obtain concentration of $BaSO_4$ in resulting fabric, a burn-off was done and found that the fabric contained 9% $BaSO_4$.

EXAMPLE 3

PMMA with $BASO_4$, High Concentration

To produce a 1:1 PMMA:$BaSO_4$ (wt./wt.) electrospun fabric, a solution was made in two components. In Jar 1, 0.5 g PMMA ($M_n$=996 kDa) was mixed in 1 mL chloroform and placed on roller to dissolve. In Jar 2, 0.5 g $BaSO_4$ (<5 um particles, as prepared above) was mixed with 1 mL chloroform, 0.5 mL dichloromethane and 50 mg TWEEN-80 and sonicated for not less than 1 hour. Just before spinning, Jar 2 was added to Jar 1 and rolled until well mixed (~5 minutes). The solution was electrospun on an electrospinning apparatus assembled in-house with the following conditions:
- 20-gauge blunt-end needle
- 0.07 mL/min flow rate
- +17 kV needle
- +10 kV directional rods to help direct fiber path
- Grounded collector
- 10" needle to collector distance To obtain concentration of $BaSO_4$ in resulting fabric, a burn-off was done and found that the fabric contained 54% $BaSO_4$.

EXAMPLE 4

PMMA Co-Spun with Polycaprolactone (PCL) into Microfiber with PCL-Rich Surface

To a jar containing 1.41 g PCL (TONE® Polymer, Dow Chemical), 0.6 g PMMA ($M_n$=996 kDa), 5 mL dichloromethane and 5 mL chloroform was added. The jar was rolled until a homogenous solution was achieved. The solution was electrospun on an electrospinning apparatus assembled in-house with the following conditions:
- 20-gauge blunt-end needle
- 0.1 mL/min flow rate
- +17 Kv needle
- +10 Kv directional rods to help direct fiber path
- Grounded collector
- 10" needle to collector distance The material was shown to have PCL on the fiber surface by ATR-FTIR

EXAMPLE 5

Preparation of Bone Cement with Electrospun Radiopaque Fibers

Radiopaque bone cement was prepared using the components shown below as per the protocol noted below.
Powder Component:
- 0.8 g of electrospun material with 50% $BaSO_4$, as prepared above
- 1.2 g PMMA ($M_n$=996 kDa)
- Benzoyl peroxide Liquid Component:
- 1.688 g Methyl methacrylate monomer
- 0.2618 g Butyl methacrylate monomer
- 0.0497 g n-n-dimethyl-p-toluidine
- 0.039 mg Hydroquinone The liquid component was poured onto the powder component in a 50 cc syringe with the needle end capped. It was then mixed until homogenous with a metal spatula (~1 min). The syringe plunger was placed back in the syringe and the bone cement mixture was ejected into a single-notched 3-point bend mold for final curing at 37° C. in a 7.2pH 100 mM phosphate buffer.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An antimicrobial, radiopaque, bone cement comprising a polymeric methacrylate matrix reinforced with electrospun microfibers, wherein the electrospun microfibers comprising an anion-bearing methacrylate copolymeric chain, the anions of the copolymeric chain ionically conjugated with at least one antimicrobial agent and at least one micro-/nanoparticulate radiopacifier.

2. An antimicrobial, radiopaque, bone cement as in claim 1 wherein the methacrylate polymer of the electrospun microfibers further contains a surfactant.

3. An antimicrobial, radiopaque, bone cement as in claim 2 wherein the microfibers are electrostatically spun from a polymer solution comprising at least one organic solvent selected from the group consisting of chloroform, dichloromethane, acetonitrile, acetone, and tetrahydrofuran.

4. An antimicrobial, radiopaque, bone cement as in claim 2 wherein the surfactant comprises TWEEN-80.

5. An antimicrobial, radiopaque, bone cement as in claim 2 wherein the methacrylate polymer of the electrospun microfibers is blended with a second polymer.

6. An antimicrobial, radiopaque, bone cement as in claim 5 wherein the second polymer comprises poly-ε-caprolactone.

7. An antimicrobial, radiopaque, bone cement as in claim 1 wherein the radiopacifier comprises at least one member selected from the group consisting of a metal oxide, barium sulfate, basic bismuth carbonate, bismuth glass, and zirconium dioxide.

8. An antimicrobial, radiopaque, bone cement as in claim 7 wherein the radiopacifier comprises barium sulfate.

9. An antimicrobial, radiopaque, bone cement as in claim 1 wherein the antimicrobial agent comprises at least one member selected from the group consisting of clindamycin hydrohloride, erythromycin-glucoheptonate, gentamicin sulfate, vancomycin, and tobramycin.

10. An antimicrobial, radiopaque, bone cement as in claim 1 wherein the methacrylate polymer matrix is formed by free-radical polymerization, using a free-radical initiator and an amine-type activator, of at least one liquid methacrylate monomer selected from the group consisting of methacrylic acid, methyl methacrylate, ethyl methacrylate, isobutyl methacrylate, hexyl methacrylate, hydroxyethyl methacrylate, and octyl methacrylate.

11. An antimicrobial, radiopaque, bone cement as in claim 10 wherein the free-radical initiator is selected from the group consisting of benzoyl peroxide and di-t-butyl peroxide, the amine-type activator comprises N,N-dimethyl-p-toluidine, and the liquid methacrylate monomer comprises hydroquinone.

12. An antimicrobial, radiopaque, bone cement as in claim 10 wherein the electrospun microfibers are in the form of a microfibrous construct selected from the group consisting of a non-woven flat fabric, rovings of non-woven yarn, ground entangled microfibers with-an. average microfiber length of less than 1 mm and compressed dense sheets of entangled microfibers having an average thickness of less than 0.5 mm.

13. A method for preparing the bone cement as in claim 12 comprising the steps of:
   a) rinsing the electrostatically spun microfiber construct with water;
   b) drying the microfiber construct;
   c) mixing the microfiber construct with about 80 percent of the at least one liquid methacrylate monomer, the liquid monomer containing the free-radical initiator;
   d) mixing the premixed combination from step c) with the remaining about 20 percent of the liquid monomer, the remaining about 20 percent containing the amine-type activator;
   e) transferring the mixture from d) to an application site; and
   f) allowing the composite to cure at about 37° C.

14. An antimicrobial, ,radiopaque, bone cement as in claim 1 wherein the methacrylate polymer matrix is formed by the free-radical polymerization of N-vinyl pyrolidone, methyl methacrylate, and one further monomer selected from the group consisting of hexyl methacrylate, methacrylic acid, isobutyl methacrylate, and octyl methacrylate.

15. An antimicrobial, radiopaque, bone cement as in claim 1 wherein the electrospun microfibers comprise organometallic microfibers.

16. An antimicrobial, radiopaque, bone cement as in claim 15 wherein the organometallic microfibers comprise an electrospun methacrylate copolymer having reactive carboxylate groups ionically conjugated with barium ions.

17. An antimicrobial, radiopaque, bone cement as in claim 1 wherein the methacrylate polymer of the matrix is blended with at least one low glass transition polyester.

18. An antimicrobial, radiopaque, bone cement as in claim 17 wherein the at least one low glass transition polyester is by condensation polymerization of a dihydroxy compound and a diester.

19. An antimicrobial, radiopaque, bone cement as in claim 17 wherein the at least one low glass transition polyester is made by the ring-opening polymerization of at least one cyclic monomer selected from the group consisting of $\epsilon$-caprolactone, l-lactide, trimethylene carbonate, p-dioxanone, glycolide, and a morpholinedione.

* * * * *